United States Patent
Lampropoulos (10) Patent No.: US 7,174,928 B1
(45) Date of Patent: Feb. 13, 2007

(54) MULTI-PART WASTE CONTAINER APPARATUS

(75) Inventor: Fred P. Lampropoulos, Sandy, UT (US)

(73) Assignee: Microsoft Corporation, Redmond, WA (US)

( * ) Notice: Subject to any disclaimer, the term of this patent is extended or adjusted under 35 U.S.C. 154(b) by 0 days.

(21) Appl. No.: 11/198,634

(22) Filed: Aug. 5, 2005

(51) Int. Cl.
*B65B 1/04* (2006.01)

(52) U.S. Cl. .................... 141/311 A; 141/86; 604/110; 604/192; 206/366

(58) Field of Classification Search ............ 141/311 A, 141/86, 88, 98, 110; 604/110, 192; 206/366, 206/370
See application file for complete search history.

(56) References Cited

U.S. PATENT DOCUMENTS

| | | | | |
|---|---|---|---|---|
| 5,483,999 A | * | 1/1996 | Lampropoulos et al. | 141/86 |
| 5,707,173 A | * | 1/1998 | Cottone et al. | 405/129.55 |
| 6,053,314 A | * | 4/2000 | Pittman | 206/366 |
| 6,719,017 B1 | * | 4/2004 | McArthur et al. | 141/86 |

* cited by examiner

*Primary Examiner*—Steven O. Douglas
(74) *Attorney, Agent, or Firm*—Workman Nydegger (57) ABSTRACT

A multi-part biowaste container including a plurality of biowaste containers having a low profile design and collectively providing sufficient storage volume to accommodate the amount of blood, tissues, and other biological materials generated during a typical surgical procedure. In one embodiment, the multi-part biowaste container includes an anti-splash container, a dual purpose lid container, and a supplemental container. The use of three separate container members increases the total volume and storage capacity of the biowaste containers while minimizing the overall profile or height of the containers. The individual containers of the multi-part biowaste container can include adhesive backing allowing the containers to be secured to the surgical work surface.

34 Claims, 8 Drawing Sheets

MULTI-PART WASTE CONTAINER APPARATUS

BACKGROUND OF THE INVENTION

1. The Field of the Invention

The present invention relates to biowaste containers. In more particular, the present invention relates to a multipart biowaste container for use in a surgical setting.

2. The Relevant Technology

A great amount of attention has been focused on the appropriate disposition of blood, tissue, and other biological materials that are produced in modern surgical settings. Much of this focus results from concerns regarding contamination, possible infection, and exposure to such materials, as well as bioethical considerations directed to proper disposition of human tissues.

As a result, a number of basins and other specialized receptacles for blood, tissue, and other biological materials have been developed. Typically, during a medical procedure such blood, tissue, and biological materials are deposited into specially designed containers and/or receptacles until the completion of the procedures. After the completion of the procedure, the attending staff can then quickly and readily identify blood, tissues, and other biological materials that require special handling or special disposal procedures. The attending staff can then simply discard of the entire container without the need to separately attend to individual biowaste elements.

Some biowaste containers suffer from a number of deficiencies. For example, one problem presented by such biowaste containers is that they must be sufficiently large to accommodate the volume of biowaste that is typically produced during a typical surgical procedure. As a result, the biowaste containers must either have a fairly large footprint or have a sufficient depth to accommodate the required amount of biological waste.

Due to the fact that surgical working surfaces available to hold the biological waste container must also accommodate a number of other surgical implements, biological waste containers covering a large surface area are typically impractical. As a result, a biological waste container covering a smaller surface area but having a greater depth relative to their overall size are typically provided in such surgical settings. While biological waste containers having a greater height relative to their overall size are more practical due to surgical area surface constraints, such waste containers can be somewhat cumbersome to use. Additionally, the greater height can make it difficult to reach other tools or implements located close to the biological waste container. In some circumstances, attempts to access implements positioned adjacent the biological waste container can even result in tipping of the biological waste container when inadvertently bumped or contacted by a practitioner during surgery.

The size of such biological waste containers can also be fairly cumbersome to ship and store due their overall size. This can be particularly problematic where the biological waste container includes a lid or other secondary member. To alleviate this problem, the lids are sometimes shipped in place on the biological waste container. During preparation for surgery, the surgical staff simply removes the lid and places it to the side until the end of surgery. While this alleviates some of the problems with storage and shipping of the lid member, it can be inconvenient to find a place to store the lid during surgery. After the surgery is completed it can be difficult to locate the lid in order to place it on biological waste container for disposal.

Some biological waste container designs utilize a lid that nests on the underside of the biological waste container. During the procedure the lid remains in contact with the biological waste container until the procedure is completed. The lid can then be removed from the bottom of the biological waste container and placed over the top of the biological waste container to secure the contents of the biological waste container during disposal. Unfortunately, where the biological waste container becomes somewhat full of blood, tissue or other biological materials, removal of the lid from beneath the biological waste container can result in inadvertent spillage or other issuance of such materials from the biological waste container. As a result of the various complications and limitations of existing biological waste containers practitioners are forced to select biological waste containers having the least number of deficiencies for the type of procedure being performed. However, this can be impractical due to the purchasing constraints and storage realities inherent in hospital and surgical center economics.

BRIEF SUMMARY OF THE INVENTION

The present invention is directed to a multi-part biowaste container configured to provide a low profile design while providing sufficient storage volume to accommodate the amount of blood, tissues, and other biological materials generated during a typical surgical procedure. In one embodiment, the multi-part biowaste container includes an anti-splash container, a dual purpose lid container, and a supplemental container. The use of three separate container members increases the total volume and storage capacity of the biowaste containers while minimizing the overall profile or height of the containers.

To reduce the amount of surgical space occupied by three separate containers, the containers can be placed in various useful or convenient locations as needed during surgery. Because the containers have a relatively low profile relative to their overall size, the containers are not easily bumped or tipped during the procedure. According to one embodiment of the present invention, an adhesive pad is provided in connection with the bottom surface of one or more of the containers. The adhesive pad allows the containers to be adhered to the working surface to prevent inadvertent knocking or spilling of the container. This also allows the containers to be positioned in unconventional locations such as directly on the patient's chest or abdomen.

The anti-splash container includes a basin and a splash guard positioned to cover the basin. The basin is selected to have an overall surface area that corresponds to the surface area of biological waste containers typically used in a surgical setting. As previously discussed, the height of the wall of the basin is selected to provide an overall low profile to facilitate use of the container in a restricted surgical settings. The splash guard is provided to cover to the basin. The splash guard allows the introduction of fluid materials into the biological waste container in a manner which contains the fluids from inadvertent splashing or other release of the fluids once placed within the basin. According to one embodiment of the present invention, the splash guard includes a silt valve that allows for the introduction of blood, tissues or other biological materials into the basin in a safe and advantageous manner.

According to another embodiment of the present invention, an absorbent pad is provided in the bottom of the basin.

The absorbent pad is configured to absorb blood, fluids, and other biological materials in a manner to facilitate containment of the biological materials in the basin. The absorbent pad can include chemical properties that solidify, or coagulate the biological materials such as in a gel form to maximize the containment of such materials.

The dual purpose lid container is provided as a secondary receptacle for receiving biological materials. The dual purpose lid container has overall dimensions that are similar to the anti-splash container. For example, the dual purpose lid container has a somewhat low profile while conforming to the overall footprint typically utilized biological waste containers. The dual purpose lid container includes a pour spout positioned at a corner of the upper rim of the dual purpose lid container. The pour spout allows for controlled and advantageous drainage of any excess blood, fluid, or biological materials from the dual purpose lid container into a secondary container.

Typically such blood, fluid, or other biological materials are drained from the dual purpose lid container into the slit valve of the anti-splash container. In this manner, all biological materials are consolidated in a manner allowing the containers to be easily and quickly be disposed of through proper procedures. Once the dual purpose lid container has been appropriately drained, the dual purpose lid container is configured to fit over the anti-splash container as a secondary and reliable containment mechanism. As a result, during disposal, the anti-splash container can be handled without leakage, splashing, or spilling of blood, fluids, or other materials from the anti-splash container.

According to one embodiment of the present said invention, an absorbent pad is also provided in connection with the dual purpose lid container. The absorbent pad performs essentially the same function as the absorbent pad of the anti-splash container. In this embodiment, the overall depth of the dual purpose lid container is designed such that when the absorbent pad of the dual purpose lid container is saturated with blood, fluid, or other materials, the saturated absorbent pad does not interfere with proper operation of the dual purpose lid container in covering and cooperatively engaging the anti-splash container. According to another embodiment of the present invention, the rim of the dual purpose lid container is slightly narrower than the rim of the anti-splash container. As a result, the rim of the dual purpose lid container is not inadvertently contacted and loosened relative to the anti-splash container.

The supplementary container is provided as a tertiary receptacle for biological materials in addition to the anti-splash container and the dual purpose lid container. The supplementary container also has dimensions similar to the anti-splash container and the dual purpose lid container. According to one embodiment of the present invention, the supplementary container is not only provided as a supplementary biowaste container, but may be utilized for other surgical purposes, such as a receptacle for saline or other flushing fluids. The supplementary container may also be utilized to hold surgical instruments, or gauze pads. The supplementary container can also be designed to provide a lid for the anti-splash container in the event that the volume of fluid in the dual purpose lid container is in excess of that which can be accommodated by the anti-splash container. According to one embodiment of the present invention, the dual purpose lid container and the supplementary container also utilize adhesive pads or other gripping surfaces to minimize slippage or tipping of these containers.

The dual purpose lid container and supplementary container are configured to nest beneath the anti-splash container during shipping. By having the ability to nest beneath the anti-splash container, the dual purpose lid container and supplementary container provide an overall low profile and efficient storage volume for the multipart biowaste container. This can substantially reduce the cost of packaging and storage of the multipart biowaste containers while facilitating preparation for the surgical procedure to be performed.

Once the multipart biowaste container is ready to be utilized in the surgical setting, the anti-splash container, dual purpose lid container, and supplementary container can be separated from one another. By utilizing three separate containers, the overall storage volume of the three containers is comparable to that of other biowaste containers without encumbering substantial amounts of the working surface or interfering with the use of other instruments and materials positioned on the working surface. According to one embodiment of the present invention, the height of the walls of one or more of the anti-splash container, the dual purpose lid container, and/or the supplementary container is less than two inches. According to another embodiment, when the anti-splash container, dual purpose lid container, the supplementary container are nested one within another, the height of the multipart biowaste container is less than three inches. According to another embodiment of the present invention, the anti-splash container, the dual purpose lid container, and the supplementary container have an individual wall height that is less than 1.5 inches and a total overall height when nested for shipping of less then 2 inches.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
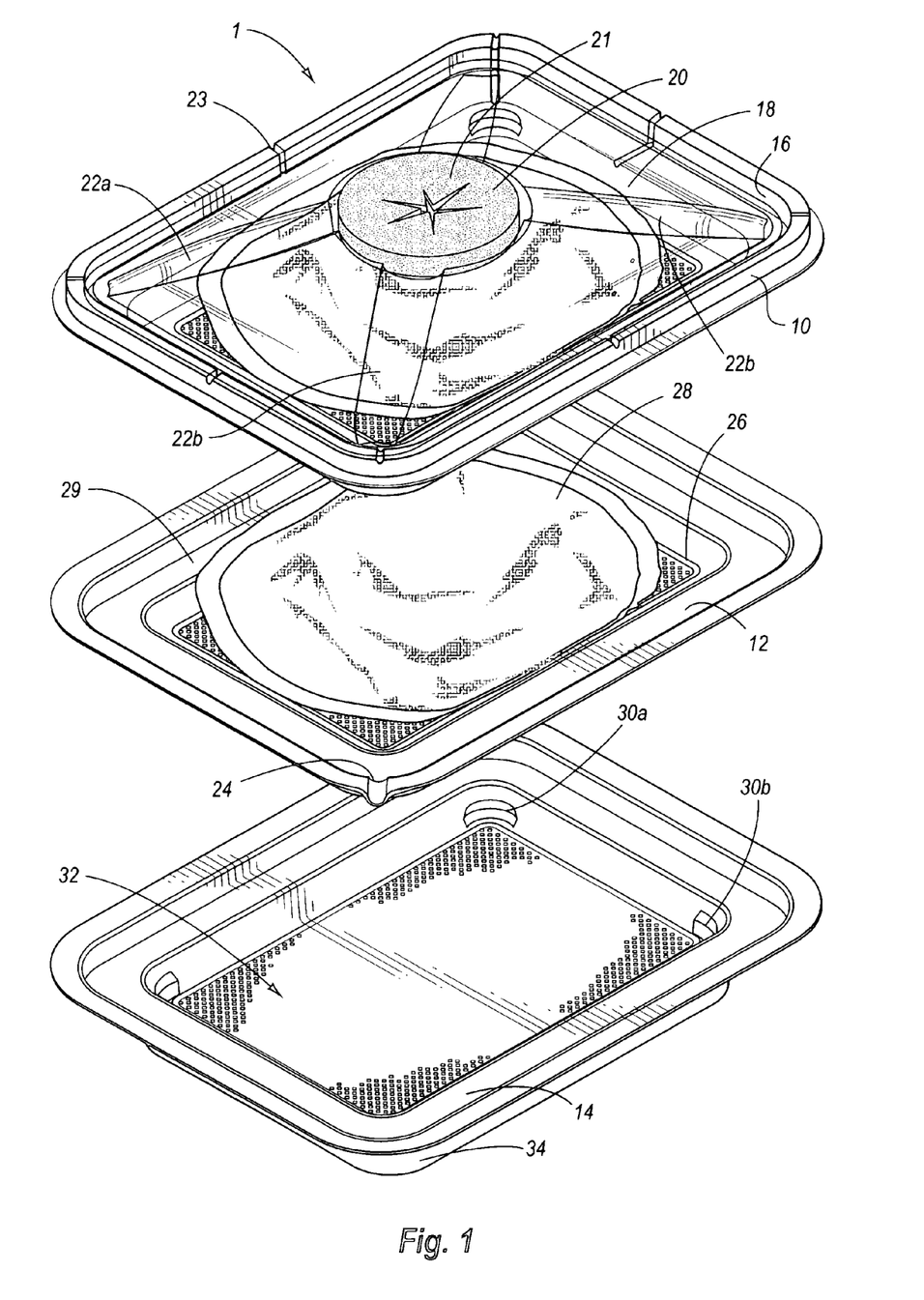
FIG. 1 is a perspective view of a multipart biowaste container illustrating an anti-splash container, a dual purpose lid container, a supplementary container.

FIG. 1 illustrates the multipart biowaste container 1 including an anti-splash container 10, a dual purpose lid container 12, and a supplementary container 14. The multipart biowaste container is configured to provide a receptacle for blood, tissue, and other biological materials that result from a surgical procedure being performed. Additionally, the multipart biowaste container 1 is designed to allow safe and effective disposal of the materials contained therein. Anti-splash container 10 is configured to allow the introduction of blood, tissues, or other biological wastes while preventing the inadvertent splashing or spillage of such materials once introduced into anti-splash container 10.

Dual purpose lid container 12 provides an additional receptacle for receiving blood, tissues, or other biological materials. Because dual purpose lid container 12 does not include an anti-splash component or other covering, larger biological materials or implements that may be used during the course of the procedure can easily be placed in dual purpose lid container 12. At the conclusion of the procedure, dual purpose lid container 12 provides a secure lid for covering anti-splash container 10. Once dual purpose lid container 12 is securely secured to the top of anti-splash container 10, dual purpose lid container 12 can then be disposed of without spillage of fluids from anti-splash container 10.

Supplementary container 14 provides yet another receptacle for receiving blood, tissues, or fluids during the course of the surgical procedure. The use of anti-splash container 10, dual purpose lid container 12, and supplementary container 14 provide the ability to hold a significant total volume of blood, tissues, or other biological materials that may be produced during the course of the procedure. By providing three separate biowaste containers, multipart biowaste container 1 also allows individual anti-splash container 10, dual purpose lid container 12, and a supplementary container 14 to be placed in strategic locations in the surgical work area. The ability to strategically locate containers 10, 12, and 14 facilitates simultaneous operation of different aspects of the procedure being performed. In the illustrated embodiment, anti-splash container 10, dual purpose lid container 12, and supplementary container 14 all have a low profile relative to their overall size, to minimize spilling, tipping, or other interference with containers 10, 12, and 14 during the course of the surgical procedure. During shipping and storage of the multipart biowaste container 1, anti-splash container 10, dual purpose lid container 12, and supplementary container 14 are nested within one another providing a single item having a relatively low profile and overall efficient storage volume.

In the illustrated embodiment, anti-splash container 10 includes a basin 16 and a splash guard 18. Basin 16 is adapted to receive and contain blood, fluids, and other biological materials that are introduced to anti-splash container 10. Basin 16 includes a multipart wall 17 and vent channels 23. Multipart wall 17 has a relief surface configured to nest with one or both of dual purpose lid container 12 and supplementary container 14. Multipart wall 17 has a height of less than two inches providing an overall low profile relative to the overall size of anti-splash container 10. This minimizes spillage or tipping of anti-splash container 10 during use. Vent channels 23 provide venting to the interior of basin 16 allowing the passage of air from the volume of basin 16 as blood, fluids, and other materials are introduced into basin 16. Additionally, the configuration of vent channels 23 minimizes the passage of fluids or other biological materials from the interior basin the exterior of basin 16.

Splash guard 18 is configured to nest within the rim of basin 16 in a simple and secure manner. Splash guard 18 provides a covering to the interior of basin 16. Splash guard 18 allows the introduction of blood, fluids, and other biological materials into basin 16 while minimizing splashing or the inadvertent spilling of materials within basin 16. Splash guard 18 includes an input site 20, a slit valve 21, and flow channels 22a, b, c, d. Input site 20 comprises a bore in the middle of the plastic material forming splash guard 18. Input site allows for the introduction of fluid and materials through the plastic guard portion of splash guard 18 and into the volume of basin 16.

Slit valve 21 is secured over the top of input site 20. Slit valve 21 permits the introduction of blood, fluids, and other biological materials through input site 20 while controlling inadvertent splashing or spillage of materials from the volume of basin 16. In the illustrated embodiment, slit valve 21 comprises a compressible foam material which allows the passage of air while minimizing the inadvertent flow of fluids from within the volume of basin 16. For example, in a catheterization procedure, a catheter is introduced through the slits of slit valve 21 and into the volume of basin 16. When the opposing end of the catheter is inserted into the patient, saline, blood, contrast media, or other fluids which may be positioned in the catheter flow directly into the volume of basin 16. Splash guard 18 and a corresponding slit valve 21 minimize the splashing of such blood, fluids, or other biological material to the external environment.

Flow channels 22a, b, c, d are provided at the four angular ridges of splash guard 18. Flow channels 22a, b, c, d originate adjacent the slit valve 21 and input site 20 and run in a funnel type fashion to the corners of splash guard 18. Flow channels 22a, b, c, d provide a contained and efficient mechanism for directing the flow of fluids that contact the exterior splash guard 18 but are not introduced into the volume of basin 16 through slit valve 21. Such blood, fluid, or other biological materials can flow along the length of flow channels 22a, b, c, d and enter the volume of basin 16 through corresponding vent channels 23.

As will be appreciated by those skilled in the art, a variety of types and configurations of anti-splash containers can be utilized without departing from the scope and spirit of the present invention. For example, a valve member not comprising a slit valve can be utilized in connection with the input site. Additionally a valve formed from elastomeric or other deformable materials can be utilized in connection with the input site. In another embodiment, the flow channels correspond with a low elevation portion of the splash guard such that the splash guard facilitates funneling of fluids not introduced through the input site. In another embodiment, the shape, size, and/or juxtaposition of elements of the anti-splash container are varied.

Dual purpose lid container 12 is provided as an additional receptacle for the containment of blood, tissues, or other biological materials. Dual purpose lid container 12 includes a pour spout 24, a waste basin 26, and absorbent pad 28.

Waste basin 26 is configured to receive and effectively hold biological materials introduced into dual purpose lid container 12. Pour spout 24 is provided at the corner of waste basin 26 to allow a practitioner to safely and efficiently pour excess fluids collected in waste basin 26 into a disposal receptacle or into anti-splash container 10. Absorbent pad 28 is provided at the inside bottom surface of waste basin 26. Absorbent pad 28 absorbs blood, fluid, or other biological materials which are introduced into dual purpose lid container 12 to effectively contain such materials within dual purpose lid container 12. According to one embodiment of the present invention, absorbent pad 28 is imbued with chemical properties which solidify, coagulate, or otherwise contain biological waste materials (such as by forming a gel or other acceptable material properties to contain such materials.) According to one embodiment of the present invention, the absorbent pad is imbued with Sodium Polyacrylate [sp?] or the equivalent.

Multipart wall 29 has an interior relief which is configured to nest on the underside of anti-splash container 10. Nesting of dual purpose lid 12 on anti-splash container 10 provides a minimal overall size and volume of multipart biowaste container 1 during shipping and storage of multipart biowaste container 1. Additionally, the overall height of multipart wall 29 is less than two inches, minimizing the potential for tipping or spillage of dual purpose lid container 12.

Because dual purpose lid container 12 does not include a splash guard, larger biological waste or materials imbued with biological waste can be received by dual purpose lid container 12. For example, a sponge utilized to absorb blood during the course of the procedure may be temporally, or permanently placed in dual purpose lid container 12. When the surgical procedure is completed, any excess blood, fluid, or other biological waste not solidified by absorbent pad 28 can be poured from waste basin 26 and into a secondary receptacle such as anti-splash container 10. The dual purpose lid container 12 can then be placed over the top and securely fastened to anti-splash container 10 to secure the biological waste during disposal of both anti-splash container 10 and dual purpose lid container 12.

The height of multipart wall 29 is designed to provide clearance between absorbent pad 28 and splash guard 18 of anti-splash container 10. When dual purpose lid container 12 is securely fastened to the top of anti-splash container 10, dual purpose lid container can accommodate splash guard 18 without interference from absorbent pad 28, even when absorbent pad 28 is saturated with blood, fluid, or other materials. The plurality of grip members 30a, b, c, d are positioned at the corners of multipart wall 17 to secure anti-splash container 10 into dual purpose lid container 12 when dual purpose lid container 12 is nested on the underside of anti-splash container 10.

Supplementary container 14 is provided as another receptacle for biological waste in addition to anti-splash container 10, and dual purpose lid container 12. Supplementary container 14 includes a liquid basin 32 and a multipart wall 34. As with anti-splash container 10 and dual purpose lid container 12, the multipart wall 34 of supplementary container 14 has sufficiently low profile to minimize spilling or tipage of materials within supplementary container 14.

Supplementary container 14 does not include an absorbent pad as depicted with dual purpose lid container 12. This allows a surgical staff to utilize supplementary container 14 for saline, flushing fluids, or other liquids that may be used during the course of the procedure. For example, in the event that a volume of saline is used early in the procedure, when minimum amounts of biological materials need to be disposed of, the surgical staff may utilize supplementary container 14 as receptacle for such saline at the early portions of the procedure. During later stages of the procedure where more biological waste is produced and needs to be disposed of, the surgical staff can utilize supplementary container 14 as a receptacle for such biological waste.

At the completion of the procedure, supplementary container 14 can be disposed of in connection with anti-splash container 10 and dual purpose lid container 12 or separately as dictated by the surgical procedure. The relief of multipart wall 34 of supplementary container 14 is designed to nest on the underside of dual purpose lid container 12 during shipping. This provides an overall low profile design to optimize shipping and storing of the multipart biowaste container 1.

As will be appreciated by those skilled in the art a variety of types and configurations of multipart biowaste containers can be utilized without departing from the scope and spirit of the present invention. For example, in one embodiment, the multipart biowaste container does not include a supplementary container but instead utilizes only an anti-splash container and a dual purpose lid container. In another embodiment, one or both of the supplementary container and dual purpose lid container are configured to nest on top of anti-splash container during shipping and storage of the multipart biowaste container. In another embodiment, both the dual purpose lid container and supplementary container include pour spouts. In yet another embodiment, the supplementary container is provided with an absorbent pad.

Figure 2:
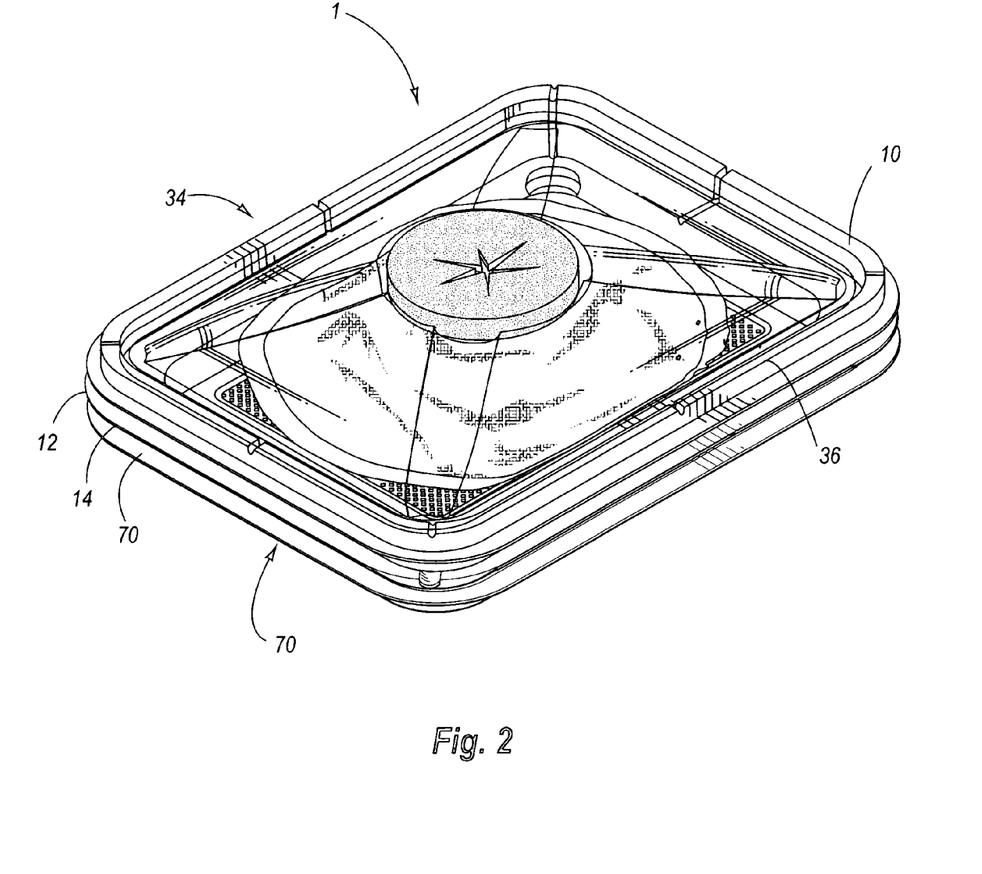
FIG. 2 is a perspective view of the multipart biowaste container in which the anti-splash container, dual purpose lid container, and supplementary container are nested together to provide an efficient volume for shipping and/or storage.

FIG. 2 illustrates multipart biowaste container 1 in which anti-splash container 10, dual purpose container 12, and supplementary container 14 are configured for shipping and storage of the multipart biowaste container 1. In the illustrated embodiment, anti-splash container is positioned on top of dual purpose lid container 12 and supplementary container 14. Positioning of anti-splash container 10 on top of the other containers can be utilized due to the use and positioning of anti-splash guard 18. In the illustrated embodiment, dual purpose lid container 12 is nested beneath anti-splash container 10. The primary visible portion of dual purpose lid container 12 when nested with supplementary container 14 and anti-splash container is limited to the outside rim of dual purpose lid container 12. Supplementary container 14 is nested beneath dual purpose lid container 12. In the illustrated embodiment, supplementary container 14 is positioned such that bottom 70 of supplementary container 14 provides the bottom contact surface for multipart biowaste container 1.

Multipart wall 34 of supplementary container 14 provides the bulk of the exposed wall surface of multipart biowaste container 1 when anti splash container 10, dual purpose lid container 12, and supplementary container 14 are nested together for shipping and storage purposes. In other words, the height of multipart wall 34 corresponds with the majority of the overall height of multipart biowaste container 1 when configured for shipping and storage purposes. In the illustrated embodiment, upper rim 36 of anti-splash container 10 is positioned as the upper contact surface of multipart biowaste container, when anti-splash container 10, dual purpose lid container 12, and supplementary container 14 are nested together for shipping and storage purposes.

In the illustrated embodiment, multipart wall 34 of supplementary container 14 has an overall height of less than two inches and multipart biowaste container 1 has an overall height of less than 3 inches when anti-splash container 10, dual purpose lid container 12, and supplementary container 14 are nested together for shipping and storage purposes. In another embodiment, multipart wall 34 of supplementary container 14 has an overall height of less than 1.5 inches and multipart biowaste container 1 has an overall height of less than two inches when anti-splash container 10, dual purpose lid container 12, and supplementary container 14 are nested together for shipping and storage purposes.

As will be appreciated by those skilled in the art, a variety of types and configurations of multipart biowaste containers can be utilized without departing from the scope and spirit from the present invention. For example, in one embodiment one or both of dual purpose lid container 12 and supplementary container 14 are configured to be positioned on top of anti-splash container 10 during shipping and storage. In another embodiment, the splash guard 18 of the anti-splash container is configured to be removed during shipping and storage of multipart biowaste container. In another embodiment, the anti-splash container is configured to be the bottom most container and nests beneath one or both of the dual purpose lid container and the supplementary container. In yet another embodiment, the multipart biowaste container only utilizes two containers rather then three containers.

Figure 3:
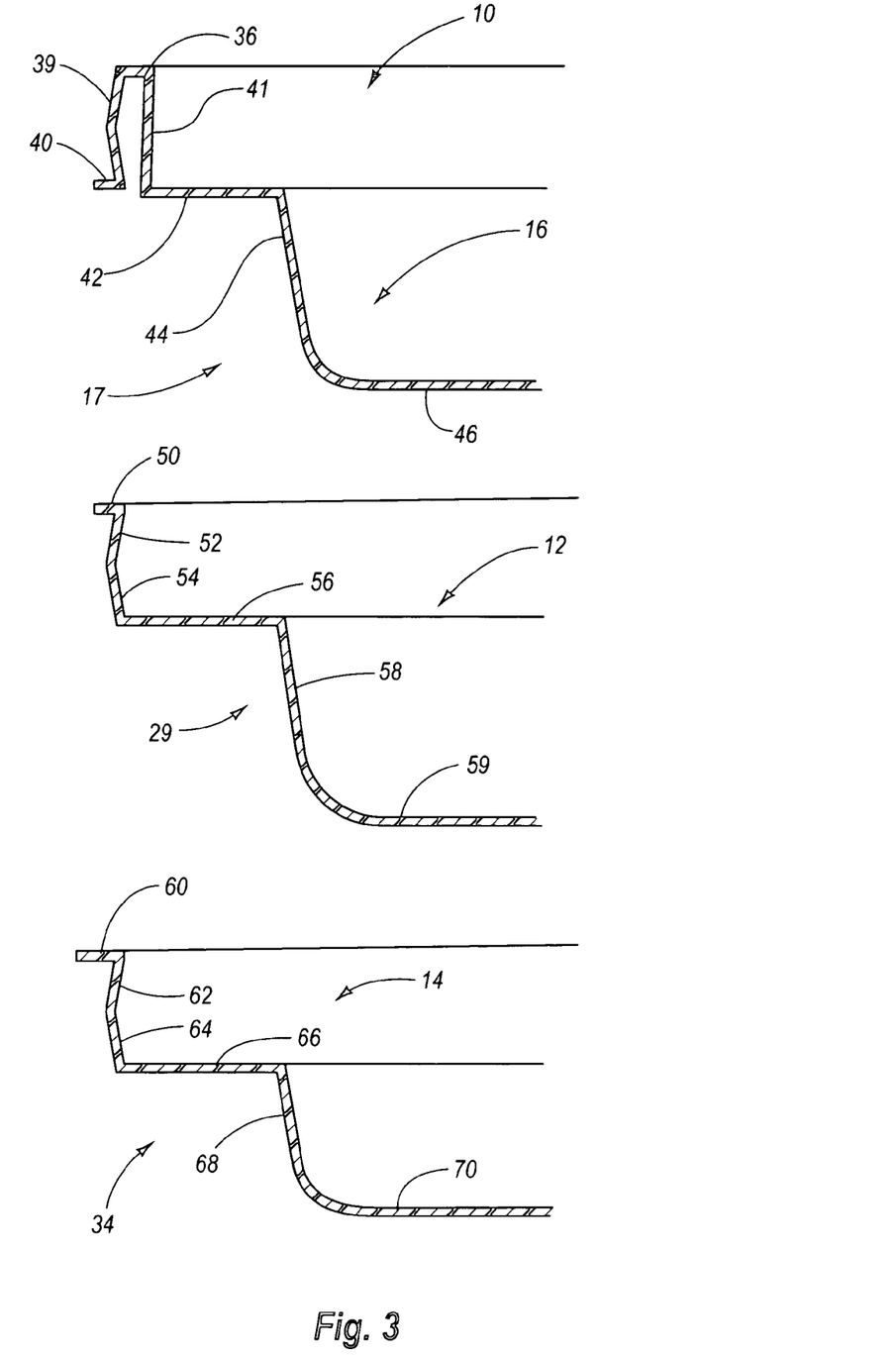
FIG. 3 is a cross-sectional partial view of the anti-splash container, dual purpose lid container, and supplementary container illustrating the profile of the walls of the containers.

FIG. 3 is a cross-sectional partial end view of anti-splash container 10, dual purpose container 12, and supplementary container 14 illustrating the relief surfaces allowing for nesting and coorperative engagement between anti-splash container 10, dual purpose lid container 12, and supplementary container 14. In the illustrated embodiment anti-splash container 10 includes an upper rim 36, an angular upper surface 39, an extension rim 40, an inner wall 41, an inner rim 42, a lower vertical wall 44, and a bottom 46.

Upper rim 36 is provided as the upper most surface of anti-splash container 10. Upper rim 36 is configured to contact a portion of dual purpose lid container 12 when dual purpose lid container 12 is cooperatively coupled to anti-splash container 10 to provide a lid for anti-splash container 10. Angular upper surface 39 is positioned adjacent and to the outside of upper rim 36. Angular upper surface 39 is configured to allow for the cooperative engagement between anti-splash container 10 and dual purpose lid container 12. Extension rim 40 extends horizontally from the volume of anti-splash container 10. Extension rim 40 abuts against dual purpose lid container 12 when the dual purpose lid container 12 is positioned over anti-splash container 10. Inner wall 41 extends downward from upper rim 36 in an angular fashion. The angular configuration of inner wall 41 secures splash guard 18 (not shown) in its correct position relative to the volume of basin 16.

Inner rim 42 extends horizontally from inner wall 41 in an inward direction. Inner rim 42 provides a bottom contact surface for splash guard 18 (not shown) securing the juxtaposition of splash guard 18 relative to basin 16. Lower vertical wall 44 extends horizontally downward from inner rim 42. Lower vertical wall 44 provides the volume of basin 16 for holding blood, fluid, or other biological materials. Bottom 46 extends horizontally from lower vertical wall 44 to provide the bottom surface of anti-splash container 10. As will be appreciated by those skilled in the art, a number of different types and configurations of multipart walls can be utilized without departing from the scope and spirit of the present invention.

Dual purpose lid container 12 is configured to nest on the underside of anti-splash container 10 during shipping and storage of the multipart biowaste container 1. In the illustrated embodiment, dual purpose lid container includes an extension rim 50, a first upper angular surface 52, a second upper angular surface 54, an inner rim 56, a lower vertical wall 58, and a bottom 59. Extension rim 50 is positioned as the upper surface of dual purpose lid container 12. Extension rim 50 extends vertically outward from the inner volume of dual purpose lid container 12. Extension rim 50 is configured to contact extension rim 40 of the anti-splash container when dual purpose lid container is positioned over anti-splash container 10 in a lid configuration.

First upper angular surface 52 extends downward and at an angle relative to extension rim 50. Second upper angular surface 54 extends downward and inward relative to first upper angular surface 52. The juxtaposition of first upper angular surface 52 and second upper surface 54 are configured to fit and facilitate engagement with angular upper surface 39 when dual purpose lid container 12 is positioned over anti-splash container 10 in a lid configuration. Inner rim 56 extends horizontally inward from second upper angular surface 54. Inner rim 56 is configured to contact upper rim 36 of anti-splash container 10 when dual purpose lid container 12 is positioned over anti-splash container 10 in a lid configuration. Lower vertical wall 58 extends downward from inner rim 56. Lower vertical wall 58 is configured to be positioned adjacent lower vertical wall 44 when dual purpose lid container is nested beneath anti-splash container 10. Bottom 59 extends horizontally inward from lower vertical wall 58.

Supplementary container 14 is configured to nest beneath dual purpose lid container 12 when multipart biowaste container 1 is being shipped and/or stored. In the illustrated embodiment supplementary container 14 includes an extension rim 60, a first upper angular surface 62, a second upper angular surface 64, an inner rim 66, a lower vertical wall 68, and a bottom 70. Extension rim 60 is positioned as the upper surface of dual purpose lid container 12. Extension rim 60 extends vertically outward from the inner volume of dual purpose lid container 12.

First angular surface 62 extends downward and at an angle relative to extension rim 60. Second angular surface 64 extends downward and inward relative to first upper angular surface 62. The juxtaposition of first upper angular surface 62 and second upper surface 64 are configured to fit and make engagement with angular upper surface 39 in the event that supplementary container 14 is positioned over anti-splash container 10 in a lid configuration. Inner rim 66 extends horizontally inward from second angular surface 64. Inner rim 66 is configured to contact upper rim 36 of anti-splash container 10 when supplementary container 14 is positioned over anti-splash container 10 in a lid configuration. Lower vertical wall 68 extends downward from inner rim 66. Lower vertical wall 68 is configured to be positioned adjacent lower vertical wall 44 when dual purpose lid container 12 is nested beneath anti-splash container 10. Bottom 70 extends horizontally inward from lower vertical wall 68.

In the illustrative embodiment supplementary container 14 is configured to be optionally utilized with anti-splash container 10 in a lid configuration. In this embodiment, in the event that both anti-splash container 10 and dual purpose lid container 12 are substantially filled with biological waste, the dual purpose lid container 12 can be disposed of and the supplementary container 14 can be utilized as a covering for the anti-splash container 10.

As will be appreciated by those skilled in the art, a variety of types and configurations of multipart walls of anti-splash container, dual purpose lid container, and supplementary container can be utilized without departing from the scope and spirit of the present invention. For example, in one embodiment, the lower vertical walls of the anti-splash container, dual purpose lid container, and supplementary container all are of similar height allowing the containers to be nested within one another. The upper angular surfaces of dual purpose lid container and supplementary container are eliminated and a secondary securement mechanism is provided to secure one or both of the dual purpose lid container and the supplementary container relative to the anti-splash container in a cover configuration.

Figure 4:
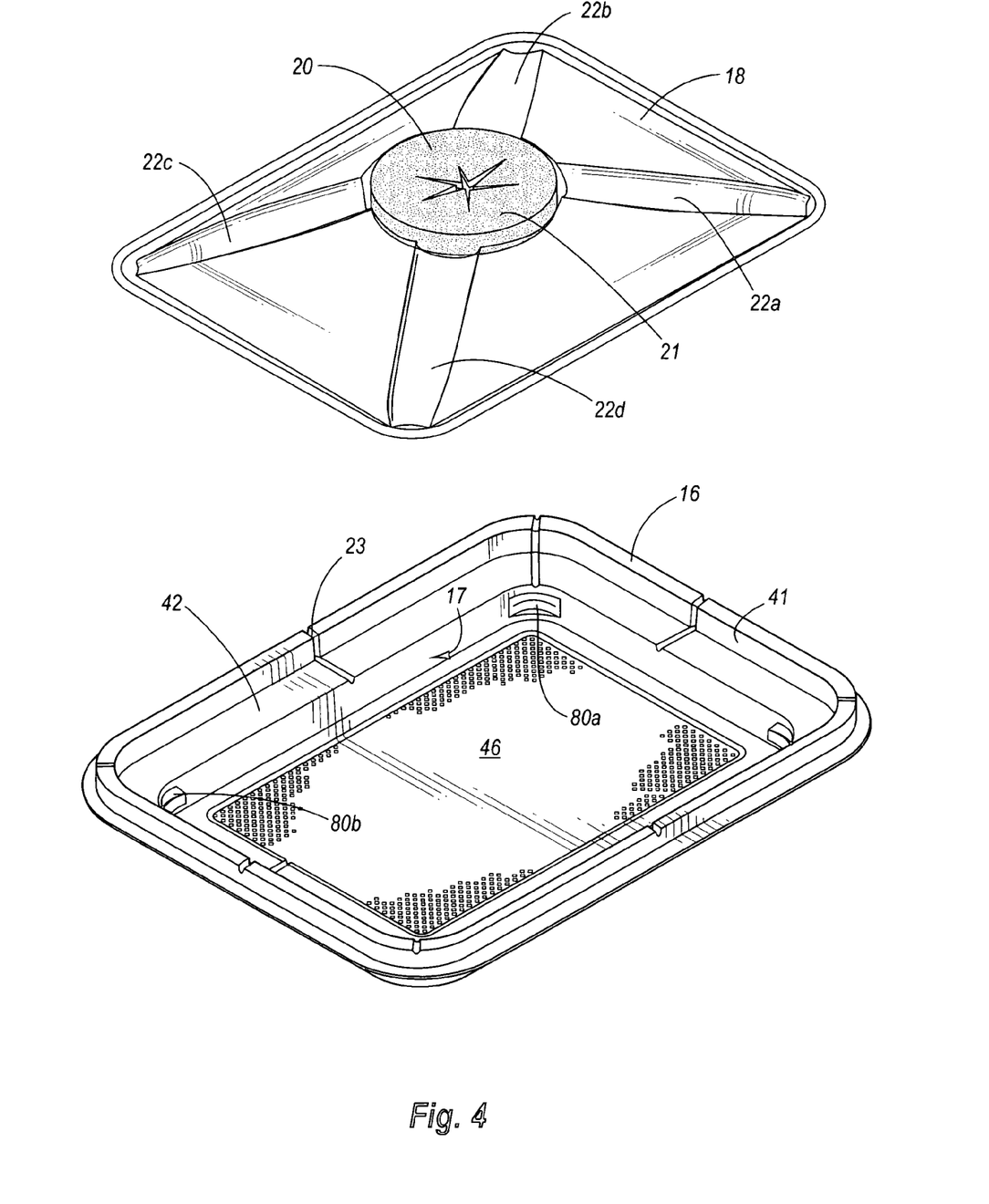
FIG. 4 is a perspective exploded view of the anti-splash container illustrating the splash guard and the basin.

FIG. 4 is a perspective view of the anti-splash container according to one embodiment of the present invention. In the illustrated embodiment, splash guard 18 is shown separated from basin 16. Splash guard 18 is clear or transparent to allow a practitioner to view the volume of materials positioned in basin 16. Splash guard 18 is configured to nest inside inner wall 41 while abutting against inner rim 42. Inner wall 41 slants slightly inward to cooperatively secure splash guard 18 without requiring a separate securement apparatus or adhesive materials.

In the illustrated embodiment, vent channels 23 are shown. Vent channels 23 provide a passageway for air and materials to facilitate passage of fluid into basin 16. In the illustrated embodiment, vent channels 23 comprise a slot on the inside surface of inner wall 41 and inner rim 42. This facilitates the passage not only past the outside rim of splash guard 18, but also to/from the volume of basin 16. Grip members 80a, b facilitate the cooperative engagement of anti-splash container 10 with the dual purpose lid container 12 and the supplementary container 14.

Figure 5:
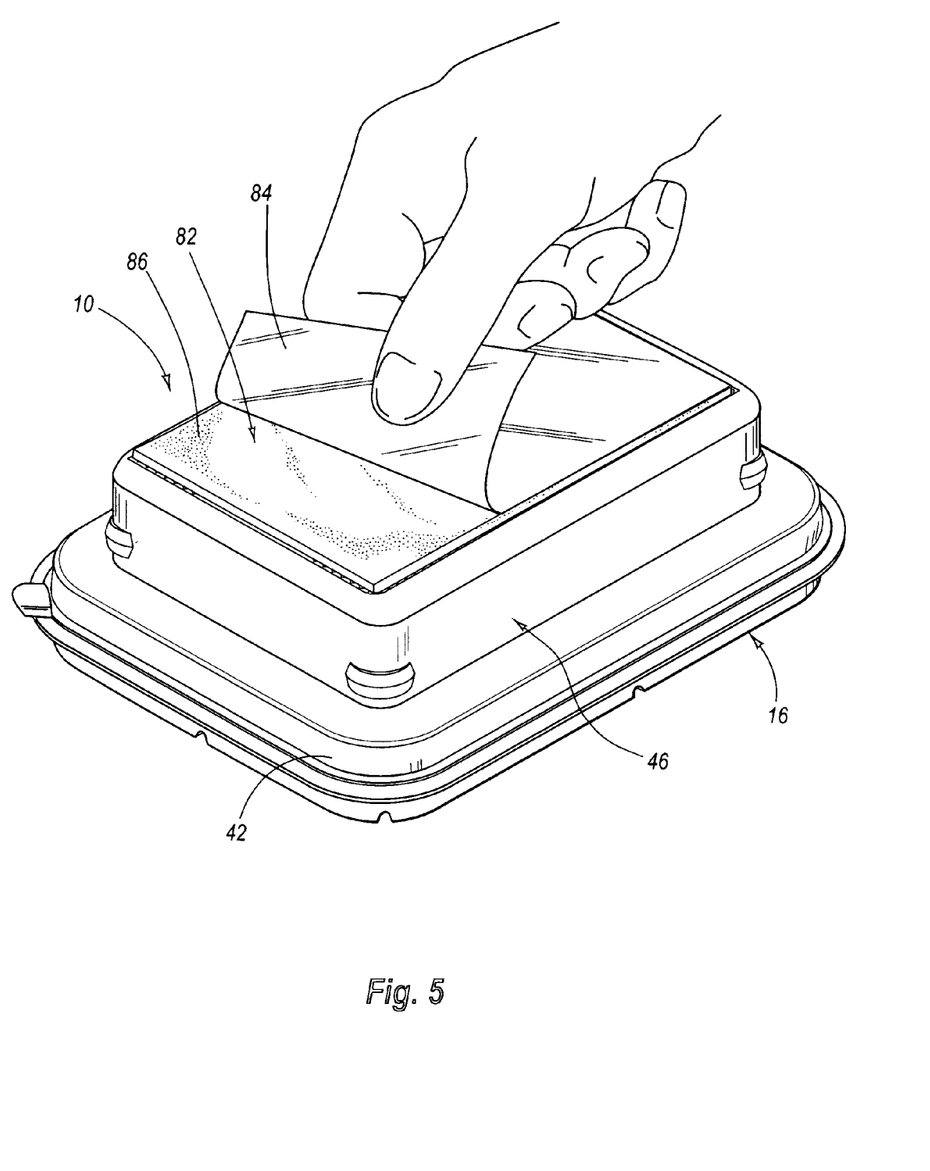
FIG. 5 is a bottom view of the anti-splash container illustrating the adhesive pad utilized to secure the anti-splash container to a working surface.

FIG. 5 is a bottom view of basin 16 of anti-splash container 10 according to one embodiment of the present invention. In the illustrated embodiment, the adhesive pad 82 is secured to bottom 46 of basin 16. Adhesive pad 82 allows the surgical staff to secure supplementary container 14 to a work surface, such as the operating table, surgical instrument support surface, or the patient, so as to minimize movement or tipping of anti-splash container 10 during surgery. Adhesive pad 82, in combination with the low-profile of anti-splash container 10, provide a safe and effective mechanism for containing biological materials introduced into anti-splash container 10 while preventing inadvertent spilling of the contents of anti-splash container 10.

In the illustrated embodiment, adhesive pad 82 includes a removable backing 84 and an adhesive layer 86. When a user is preparing to utilize adhesive pad 82, the user grasps removable backing 84 and pulls in a rearward direction. As removable backing 84 is pulled in rearward direction it separates from adhesive pad 82. Removable backing 84 maintains the adhesive properties of adhesive layer 86 prior to placement of anti-splash container 10 on the working surface. Once removable backing 84 is removed, adhesive layer 86 is exposed and can be applied directly to the work surface in which the practitioner desires to position anti-splash container 10.

As will be appreciated by those skilled in the art, a variety of types and configurations of mechanisms for maintaining the positioning of anti-splash container can be utilized without departing from the scope and the spirit of the present invention. For example, in one embodiment a hook and loop type device such as Velcro® can be positioned on the bottom of the anti-splash container. One of the hook and loop component members can be placed on the work surface and the other can be placed on bottom of the anti-splash container. The hook and loop members can then be mated to secure the anti-splash container relative to the work surface.

In another embodiment, the bottom of the anti-splash container can be textured or provided with other mechanical properties which secure the positioning of the anti-splash container to minimize tipping or spillage of the anti-splash container. As will appreciated by those skilled in the art, an adhesive pad or other acceptable alternative can be used with the dual purpose lid and the supplementary container instead of, or in addition to, that used with the anti-splash container.

Figure 6:
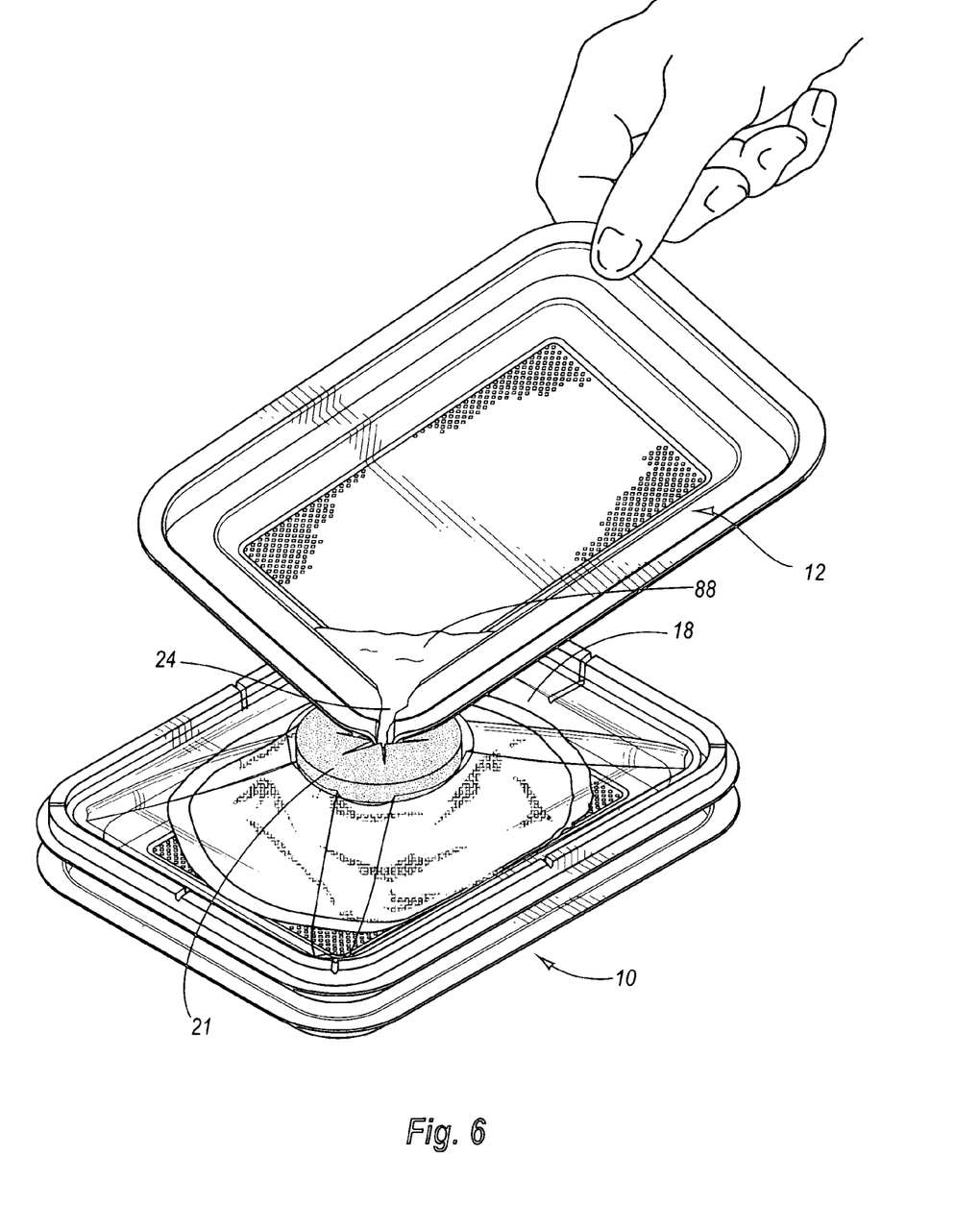
FIG. 6 is a perspective view of the anti-splash container and dual purpose lid container illustrating operation of the pour spout of the dual purpose lid container.

FIG. 6 is a perspective view of the anti-splash container 10 and dual purpose lid container 12 illustrating the manner in which materials can be poured from the dual purpose lid container 12 into the anti-splash container 10. In the illustrated embodiment, a volume of fluid 88 is positioned in dual purpose lid container 12. For one or a variety of reasons a user may desire to empty the volume of fluid 88 from dual purpose lid container 12 into anti-splash container 10. For example, at the end of the procedure the user may desire to position dual purpose lid container 12 over anti-splash container 10 in a lid configuration as previously discussed. Alternatively, the user may simply desire to consolidate all biological waste in a single container at the end of the procedure.

To drain the volume of fluid 88 from dual purpose lid container 12 the user tilts dual purpose lid container 12 in an angular fashion such that pour spout 24 is at a lower elevation than the other corners of dual purpose lid container 12. As the user tips dual purpose lid container 12, the volume of fluid consolidates at the corner of the basin corresponding with pour spout 24. As the user continues to tilt dual purpose lid container 12 the volume of fluid begins to flow through pour spout 24 to the exterior of dual purpose lid container 12.

In the illustrated embodiment, the user has begun to tilt dual purpose lid container 12. The user has simultaneously positioned pour spout 24 inside slit valve 21 such that the pour spout 24 has opened the slits of slit valve 21. The opening of slit valve 21 allows the passage of the fluids flowing from pour spout 24. In other words, fluids pour directly from pour spout 24, through slit valve 21, and into basin 16. This provides a simple and effective mechanism for transferring fluids from dual purpose lid container 12 into anti-splash container 10. Once the volume of fluid 88 has been completely drained from dual purpose lid container 12 into anti-splash container 10, dual purpose lid container 12 can be positioned over anti-splash container 10 in a lid-like fashion.

Figure 7:
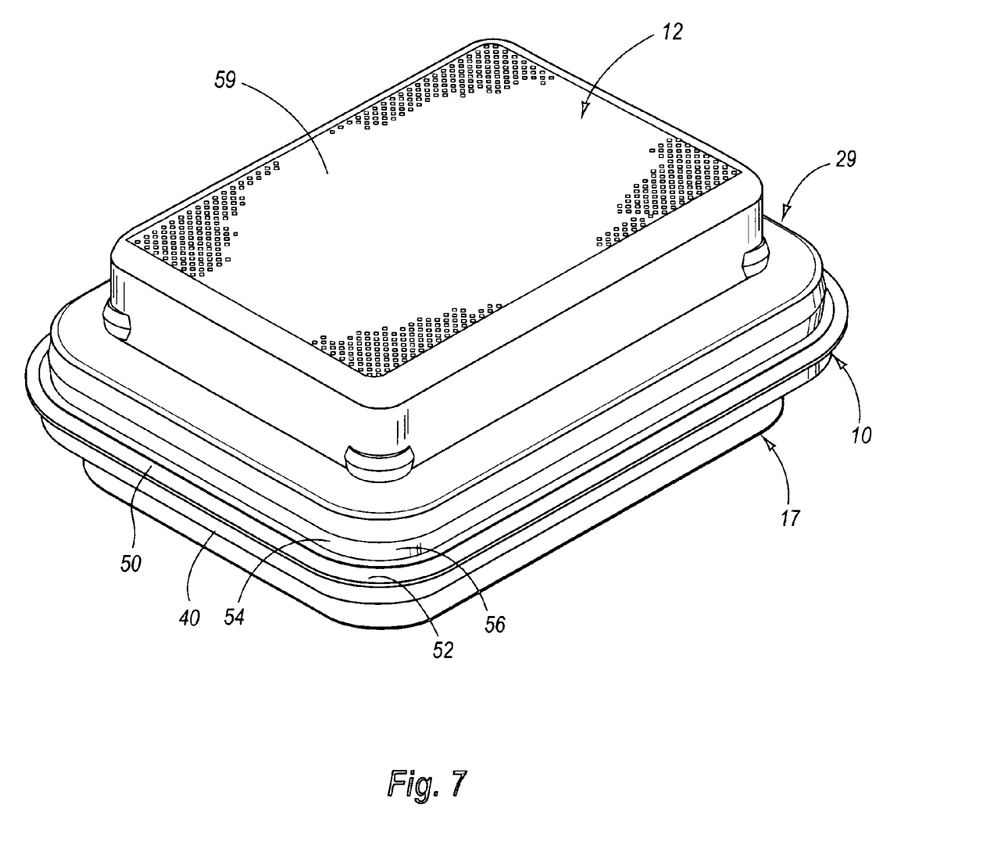
FIG. 7 is a perspective view of the dual purpose lid container secured as a covering to the anti-splash container in preparation for disposal of the anti-splash container.

FIG. 7 illustrates the juxtaposition of dual purpose lid container 12 and anti-splash container 10 when dual purpose lid container 12 has been positioned over anti-splash container 10 in a lid-like fashion. In the illustrated embodiment, dual purpose lid container 12 has been turned upside down such that bottom 59 is facing in an upwards direction. The extension rim 50 of dual purpose lid container 12 is positioned directly in contact with extension rim 40. Extension rim 50 extends outward a lesser amount than extension rim 40 making it difficult for a user to inadvertently grasp extension rim 50 and separate it from extension rim 40. This provides an efficient and reliable securement between dual purpose lid container 12 and anti-splash container 10.

First upper angular surface 52 and second upper angular surface 54 are positioned adjacent extension rim 50. First upper angular surface 52 and second upper angular surface 54 provide proper engagement with angular upper surface 39 (not shown) of anti-splash container 10. Inner rim 56 of dual purpose lid container 12 is positioned in contact with upper rim 36 (not shown) of dual purpose lid container 12.

The overall height of anti-splash container 10 in combination with dual purpose lid container 12 is slightly less than the sum of the height of multipart wall 17 of anti-splash container 10 and multipart wall 29 of dual purpose lid container 12. This is due to the overlap and cooperative engagement between first upper angular surface 52 second upper angular surface 54 of dual purpose lid container 12 and angular upper surface 39 (not shown) of anti-splash container 10.

Figure 8:
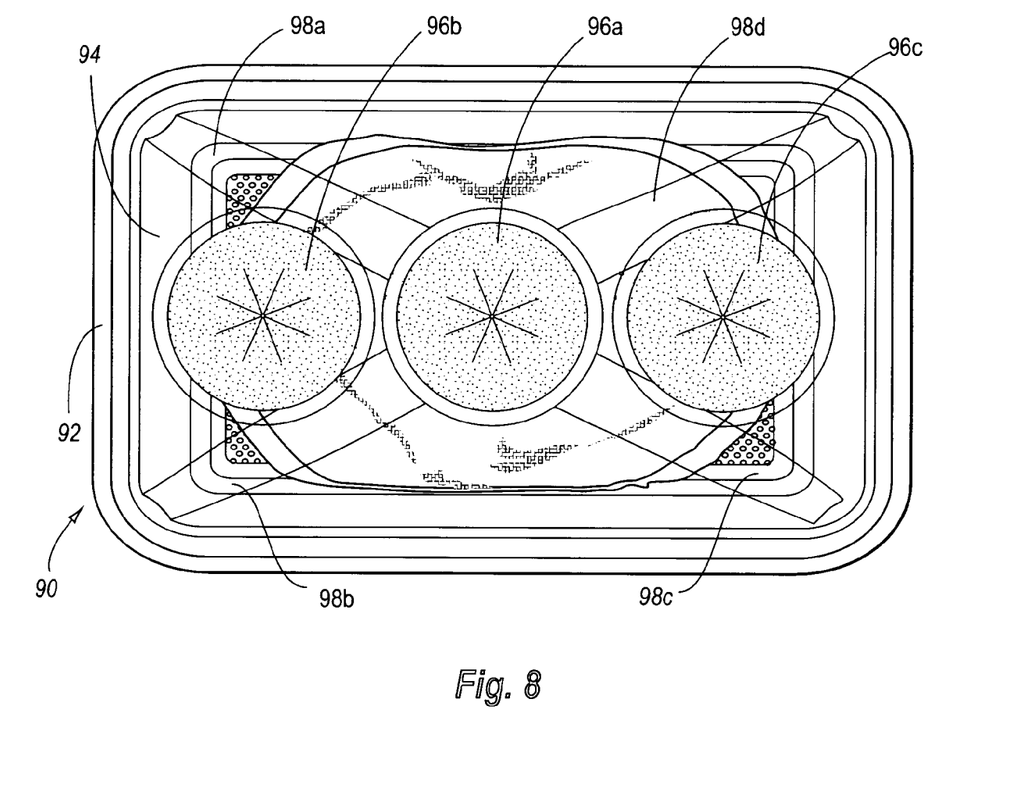
FIG. 8 is a top view of an alternative embodiment of the anti-splash container according to one embodiment of the present invention.

FIG. 8 is a top view of an anti-splash container 90 according to an alternative embodiment of the present invention. In the illustrated embodiment, anti-splash container 90 includes a basin 92, a splash guard 94, slit valves 96*a–c*, and flow channels 98*a–d*. Basin 92 is utilized to provide a receptacle to receive and contain blood, fluids, and other biological materials resulting from the surgical procedure being performed. Splash guard 94 is positioned over basin 92 to provide a cover to prevent spilling or splashing of fluids and other materials positioned in basin 92.

Slit valves 96*a–c* are positioned on the upper surface of splash guard 94. By providing a plurality of slit valves, a user can deposit blood, fluid, or other materials into basin 92 in the position or from the angle that is most convenient during the procedure. For example, it may be easier to insert the catheter through the slit valve 96*a* which is positioned centrally and at the top of splash guard 94. However, it may be more advantageous to pour fluids from dual purpose lid container 12, as depicted in FIG. 6 through one of the side slit valves 96*b* or 96*c*. Additionally, utilizing a plurality of slit valves allows multiple aspects of the procedure to be performed simultaneously. For example, one end of the catheter may be positioned through slit valve 96*a* while a practitioner is pouring fluid from dual purpose lid container 12 (not shown) through one of slit valves 96*b–c*. In the illustrated embodiment, slit valves 96*b, c* are positioned at a slight angle corresponding with the angle of the tapered side surfaces of splash guard 94.

Flow channels 98*a–d* are positioned along the ridges flowing from slit valve 96*a* to the corners of splash guard 94. Slit valves 96*b–c* are positioned between flow channels 98*a, b, c, d* such that the positioning of slit valves 96*b–c* do not interfere with operation of flow channels 98*a, b, c, d*. As will be appreciated by those skilled in the art, a variety of types and configurations of multipart biowaste containers can be utilized without departing from the scope and spirit of the present invention. For example, the anti-splash container can utilize only first and second slit valves positioned on alternate sides of the splash guard. In another embodiment, more than three waste containers are provided as part of the multi-part biowaste container. For example, first and second anti-splash containers can be nested within one another with one of the splash guards being removable and replaceable in preparation for a procedure to be performed. Additionally, first and second dual purpose lid containers can be included to nest beneath the first and second anti-splash containers providing four total waste receptacles and two anti-splash container dual purpose lid container combinations which can be disposed of separately subsequent to the completion of the procedure.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A multipart biowaste container system configured to provide a low profile design while providing sufficient storage volume to accommodate the amount of blood, tissues, and other biological materials generated during a typical surgical procedure, the multipart biowaste container comprising:
    a first biowaste container adapted to accommodate blood, fluids, and other biological waste material, the first biowaste container comprising:
        a basin for holding the blood, fluids, and other biological material introduced into the first biowaste container; and
        a cover positioned over the basin to minimize splashing or spilling of materials positioned in the basin while providing an opening to allow passage of blood, fluids, and other biological materials through the cover into the basin; and
    a second biowaste container adapted to accommodate blood, fluids, and other biological waste material, the second biowaste container comprising:
        a basin adapted to accommodate the blood, fluids, and other biological waste material introduced into the second biowaste container, the basin having a multipart wall adapted to nest with the basin of the first biowaste container during shipping and storage of the multipart biowaste container while also being adapted to be secured in a lid configuration to the first biowaste container to retain the materials in the first biowaste container during disposal; and
        an absorbent member positioned within the basin to retain blood, fluids, and other biological waste material within the second biowaste container.

2. The multipart biowaste container of claim 1, further comprising a third biowaste container configured to nest with one or both of the first biowaste container and the second biowaste container.

3. The multipart biowaste container of claim 2, wherein the third biowaste container is adapted to be secured to at least one of the first biowaste container and the second biowaste container in a lid configuration.

4. The multipart biowaste container of claim 1, wherein the cover of the first biowaste container comprises a splash guard.

5. The multipart biowaste container of claim 4, wherein the cover includes a valve associated with the opening to facilitate passage of blood, fluids, and other material into the basin while minimizing splashing of such materials.

6. The multipart biowaste container of claim 1, further comprising an adhesive member secured to the bottom of at least one of the first biowaste container and the second biowaste container.

7. The multipart biowaste container of claim 6, wherein the adhesive member secures the at least one of the first biowaste container and the second biowaste container to the surgical work surface to minimize tipping of the container.

8. The multipart biowaste container of claim 1, wherein the height of the multipart wall of the second biowaste container minimizes contact between the absorbent member of the second biowaste container and the cover of the first biowaste container when the second biowaste container is secured to the first biowaste container in a lid configuration.

9. The multipart biowaste container of claim 8, wherein the absorbent member includes chemical properties which solidify blood, fluids, and other liquids introduced into the basin of the second biowaste container.

10. A multipart biowaste container system configured to provide a low profile design while providing sufficient storage volume to accommodate the amount of blood, tissues, and other biological materials generated during a typical surgical procedure, the multipart biowaste container comprising:
   a first biowaste container adapted to accommodate blood, fluids, and other biological waste material, the first biowaste container having a length of at least 3.5 inches, a width of at least 2.5 inches, and a height of no more than 2.0 inches; and
   one or more secondary biowaste containers adapted to accommodate blood, fluids, and other biological waste material, the one or more secondary biowaste containers having a length of at least 3.5 inches, a width of at least 2.5 inches, and a height of no more than 2.0 inches, wherein at least one of the one or more secondary biowaste containers is configured to be secured to the first biowaste container in a lid fashion to retain the contents of the first biowaste container during disposal, and wherein the first biowaste container and the secondary biowaste containers are configured to nest within one another to minimize the size of the multipart biowaste container system during shipping and storage and when the first biowaste container and the one or more secondary biowaste containers are separated from one another the containers being configured to provide sufficient storage volume to accommodate the amount of blood, tissues, and other biological materials generated during a typical surgical procedure.

11. The multipart biowaste container of claim 10, wherein the first biowaste container comprises an anti-splash container.

12. The multipart biowaste container of claim 10, wherein at least one of the one or more secondary biowaste containers comprise a dual purpose lid container.

13. The multipart biowaste container of claim 10, wherein at least one of the one or more secondary biowaste containers comprise a supplementary container.

14. The multipart biowaste container of claim 10, wherein at least one of the first biowaste container and the one or more secondary biowaste containers have a length of at least four inches, a width of at least three inches and a height of no more than 1.5 inches.

15. The multipart biowaste container of claim 10, wherein the first biowaste containers and the one or more secondary biowaste containers have a total overall height when nested for shipping of less than 2 inches.

16. The multipart biowaste container of claim 10, wherein the first biowaste container includes a cover adapted to minimize splashing or spilling of the contents of the multipart biowaste container.

17. The multipart biowaste container of claim 16, further comprising one or more vent channels in connection with the cover.

18. The multipart biowaste container of claim 17, wherein the one or more vent channels allow passage of gases into and out of the biowaste container.

19. The multipart biowaste contaniner of claim 18, wherein the cover comprises one or more flow channels to facilitate passage of blood, fluids, or other materials from the outside surface of the cover to the interior of the biowaste container.

20. A multipart biowaste container system configured to provide a low profile design while providing sufficient storage volume to accommodate the amount of blood, tissues, and other biological materials generated during a typical surgical procedure, the multipart biowaste container comprising:
   a first biowaste container adapted to accommodate blood, fluids, and other biological waste material, the first biowaste container comprising:
      a basin for holding the blood, fluids, and other biological material introduced into the first biowaste container;
      a cover positioned over the basin to minimize splashing or spilling of materials positioned in the basin while providing an opening to allow passage of blood, fluids, and other biological materials through the cover into the basin; and
      an adhesive member attached to a bottom of the basin to secure the basin to a surgical work surface to minimize tipping of the basin during surgery; and
   a dual purpose lid means for accommodating blood, fluids, and other biological waste material during a surgical procedure while also being adapted to be secured in a lid configuration to the first biowaste container to retain the materials in the first biowaste container during disposal.

21. The multipart biowaste container of claim 20, wherein the adhesive member comprises an adhesive layer.

22. The multipart biowaste container of claim 20, wherein the adhesive member comprises an adhesive pad.

23. The multipart biowaste container of claim 20, wherein the dual purpose lid means comprises a secondary biowaste container.

24. The multipart biowaste container of claim 20, wherein the dual purpose lid means is configured to nest with the first biowaste container during shipping and storage of the multipart biowaste container.

25. The multipart biowaste container of claim 23, wherein the secondary biowaste container includes a pour channel.

26. The multipart biowaste container of claim 25, wherein the pour channel is adapted to facilitate transition of fluids from the interior of the secondary biowaste container to the first biowaste container.

27. The multipart biowaste container of claim 26, wherein the pour channel comprises pour spout positioned at a top corner of the secondary biowaste container.

28. A multipart biowaste container system comprising
   an anti-splash container comprising a basin adapted to accommodate blood, fluid, and other materials resulting from a surgical procedure;
   a dual purpose lid container adapted to accommodate blood, fluid, and other materials resulting from a surgical procedure while also being configured to be secured on the anti-splash container as a lid;
   a supplementary container, wherein the anti-splash container, dual purpose lid container; and supplementary container are configured to nest within one another to provide a low profile design while providing sufficient storage volume to accommodate the amount of blood, tissues, and other biological materials generated during a typical surgical procedure.

29. The multipart biowaste container of claim 28, wherein the anti-splash container includes a splash guard to minimize splashing or spilling of fluids from the anti-splash container.

30. The multipart biowaste container of claim 29, wherein the splash guard includes at least one input site to allow the passage of blood, fluids, and other materials into the anti-splash container.

31. The multipart biowaste container of claim 30, wherein the splash guard includes and at least one valve member associate with the at least one input site.

32. The mutlipart biowaste container of claim 31, wherein the at least one valve member comprises a slit valve.

33. The multipart biowaste container of claim 29, wherein the splash guard includes a plurality of input sites to allow the passage of blood, fluids, and other materials into the anti-splash container.

34. The multipart biowaste container of claim 33, wherein the splash guard includes a plurality of valve members associate with the at least one input site.

* * * * *

UNITED STATES PATENT AND TRADEMARK OFFICE
CERTIFICATE OF CORRECTION

PATENT NO. : 7,174,928 B1  Page 1 of 1
APPLICATION NO. : 11/198634
DATED : February 13, 2007
INVENTOR(S) : Fred P. Lampropoulos It is certified that error appears in the above-identified patent and that said Letters Patent is hereby corrected as shown below:

Title Page
Item 73, Assignee, change "Microsoft Corporation, Redmond, WA (US)" to
--Merit Medical Systems, Inc. South Jordan, UT (US)--

Signed and Sealed this

Fourth Day of March, 2008

JON W. DUDAS
*Director of the United States Patent and Trademark Office*